US 8,158,361 B2

Apr. 17, 2012

(12) United States Patent
Lankiewicz

(10) Patent No.: US 8,158,361 B2
(45) Date of Patent: Apr. 17, 2012

(54) TUMOR MARKER

(75) Inventor: Silke Lankiewicz, Langenhagen (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 12/700,025

(22) Filed: Feb. 4, 2010

(65) Prior Publication Data

US 2010/0216148 A1 Aug. 26, 2010

Related U.S. Application Data

(63) Continuation of application No. 11/952,006, filed on Dec. 6, 2007, now abandoned.

Foreign Application Priority Data

Dec. 6, 2006 (EP) .................................. 06025220

(51) Int. Cl.
*C12Q 1/68* (2006.01)
*C12N 15/00* (2006.01)

(52) U.S. Cl. .................... 435/6.14; 435/6.1; 435/455
(58) Field of Classification Search ............. 435/6.1, 435/6.14, 455
See application file for complete search history.

(56) References Cited

OTHER PUBLICATIONS

Kuan et al. Endocrine-Related Cancer 8:83-96, 2001.*
GenBank Accession No. AF288738, EMBL-EBI Online printout dated Feb. 5, 2007 pp. 1-59.
GenBank Accession No. P00533, UnitProtKB/Swiss-Prot printout dated Feb. 5, 2007 pp. 1-16.
Kuan et al., "EGF mutant receptor vIII as a molecular target in cancer therapy", Endocr. Relat. Cancer, 8:83-96, 2001.
Reier and Maihle, "Characterization and expression of novel 60-kDa and 110-kDa EGFR isoforms in human placenta", Ann. N.Y. Acad. Sci., 995:39-47, 2003.
Reiter et al., Comparative genomic sequence analysis and isolation of human and mouse alternative EGFR transcripts encoding truncated receptor isoforms:, Genomics, 71:1-20, 2000.

* cited by examiner

*Primary Examiner* — Marcia S Noble
(74) *Attorney, Agent, or Firm* — Fanelli Haag & Kilger PLLC

(57) ABSTRACT

The present invention concerns a gene product largely homologous to the epithelial growth factor receptor (EGFR). It further refers to mRNA coding for such epithelial growth factor receptor. The present invention provides such an epithelial growth factor receptor which is characterized in that either exons 12 to 14 or exons 12 to 15 are deleted. These novel variants of the epithelial growth factor receptor can be used for a diagnosis, stratification, therapy guidance of a tumor or therapy guidance of tumor surgery.

6 Claims, No Drawings

TUMOR MARKER

CROSS-REFERENCE TO RELATED PATENT APPLICATIONS

This application is a Continuation of U.S. application Ser. No. 11/952,006, filed Dec. 6, 2007, which is based upon and claims the benefit of priority from prior European Patent Application No. 06025220.2, filed Dec. 6, 2006, the entire contents of all of which are incorporated herein by reference in their entirety.

The instant application contains a Sequence Listing which has been submitted via EFS-Web and is hereby incorporated by reference in its entirety. Said ASCII copy, created on Mar. 29, 2011, is named 05123002.txt and is 23,449 bytes in size.

BACKGROUND OF THE INVENTION

The present invention concerns a gene product largely homologous to the epithelial growth factor receptor (EGFR). It further refers to mRNA coding for such epithelial growth factor receptor. Further, the present invention concerns the use of such a gene product as tumor marker, particularly for epithelial tumors like colon cancer, lung cancer, prostate cancer, breast cancer or other solid tumors.

Histochemical studies of primary tumors often neglect the fact that in normal and tumor cells, different variants (also called derivatives or mutants) of therapy target genes, e.g. EGFR DNA rearrangement, EGFR transcription and/or protein variants exist. The growth factor receptor EGFR is of special importance in most epithelial tumors like colon cancer, lung cancer, prostate cancer or breast cancer, because expression in primary tumors correlates with a shorter survival time/rate. Therefore, an expression of EGFR is a prerequisite for EGFR based therapy (antibodies like Erbitux or receptor tyrosine kinase inhibitors like Iressa). But about 30% of patients do not respond to antibody therapies. The reason could be that a part of the N-terminal domain of die EGFR is deleted as has been described for the variant EGFRvIII. These variants e.g. naturally occurring through alternative splicing or in tumor cells through somatic mutation) exist in the whole EGFR sequence. Soluble proteins arise without cytosolic C-terminal ends as well as membrane anchored proteins without the N-terminal ligand-binding domain. Tumor-specific variants of EGFR have been described, for example, in Kuan et al., 2001 Endocr. Relat. Cancer 8, 83-96: "EGF mutant receptor vIII as a molecular target in cancer therapy".

Variant vIII is the most abundant in different tumors such as breast or ovarian cancer but not all tumors express this variant (e.g. small cell lung carcinoma (SCLC)).

Another set of variants are short deletions (<10 amino acids) or single nucleotide mutations in the receptor tyrosine kinase domain of the EGFR that are expressed in tumor cells in non-small cell lung carcinoma (NSCLC) or neuroblastoma.

Today, two new classes of therapies exist: (1) antibodies that compete with the ligands of EGFR for example EGF or TGF-α and block the N-terminal binding domain of the receptor (Erbitux) and (2) small molecular weight receptor tyrosine kinase inhibitors (Iressa, Tarceva) that bind to the intracellular receptor tyrosine kinase domain and block the ATP binding site reversibly or irreversibly. Both therapies eliminate signal transduction of the wild-type EGFR.

But the clinical experience shows that not all patients (about 20%) respond to such therapies even if the primary tumor was tested positive for EGFR expression by IHC and/or amplification with FISH. On the other hand, patients, which were tested negative with immunohistochemical methods, sometimes respond to Erbitux therapy. One reason can be that not all patients express the wild-type EGFR but some of the EGFR variants.

Variants without the N-terminal binding domain (e.g. variant III) do not bind Pantimumab. EGFR variants without somatic mutations in the receptor tyrosine kinase domain need higher doses of, for example Iressa, to block the whole signal transduction of the EGFR. Thus, Iressa or Tarceva have a pronounced effect in NSCLC patients with single nucleotide mutations. Some new antibodies against different EGFR variants (e.g. EGFRvIII) are in preclinical studies.

DETAILED DESCRIPTION

The present invention addresses the problem of different EGFR variants existing in tumors and normal cells. It is the object of the present invention to provide improved diagnosis, stratification and/or therapy guidance of a tumor.

This object is solved by the gene product according to claim 1, the gene according to claim 8, the polynucleotide according to claim 9, the methods according to claims 15 and 16 and their use. Further improvements and modifications of the gene product, the gene, the polynucleotide and the methods are given in the respective dependent claims.

The present invention for the first provides two new EGFR variants which are preferentially expressed in tumor cells. This concerns primarily epithelial tumors, like colon cancer, lung cancer, prostate cancer or breast cancer or any other solid tumor. The new EGFR variants allow the detection of tumor cells even if present detection methods fail. They, therefore, provide improved detection of tumors, improved stratification of tumors and provide the possibility to improve therapy guidance of a tumor therapy or a therapy after tumor surgery or use the gene or gene product as target for therapeutical intervention, e.g. by antibodies, antisense RNA etc.

The newly provided EGFR variants show deletions of exons 12 to 14 (EGFR c.EX12_14del) or exons 12 to 15 (EGFR c.EX12_15del). Such variants have not been described up to date and have not been correlated to tumor cells. As will be shown in the following examples, the new EGFR variants are closely related to tumor cells and therefore provide novel tumor markers. The same is true for the mRNA coding for the new EGFR variants.

To summarize, the present invention provides new EGFR genomic or splice variants that allow identifying cancer patients since these variants are not expressed in healthy donors. It is further possible to detect cancer patients with a high risk of not responding to certain antibody therapies directed towards the N-terminals of the EGFR protein.

These new EGFR variants therefore allow for the detection of the presence of a tumor by analyzing a sample for the presence of the novel EGFR variants. As sample, any kind of sample like tissue sample, body fluid sample, like blood samples and the like, are suitable. Of course, samples derived from the primary tumor or from micrometastases are also well suited to stratify the tumor and influence therapy guidance for this tumor before or after tumor surgery.

In the following, examples for isolation of the novel EGFR variants as well as their statistical detection in tumor samples are provided.

The new EGFR variants were isolated from mRNA of neuronal cell lines of the brain (U87MG and U251) by RT-PCR with a primer pair with the following sequences: forward primer: 5'AAACTGCACCTCCATCAGTG3' (SEQ ID NO:6) and reverse primer: 5'ATTCGTTGGACAGCCT-TCAAG3' (SEQ ID NO:7) under the following conditions:

95° C., 15 min., (94° C., 30 s, 60° C., 30 s, 72° C., 1 min.) for 45 cycles, 72° C., 5 min; 0.5-1 μM of each primer and HotStarTaq Mix (Qiagen GmbH, Hilden, Germany) in a volume of 50 μl. By using this primer pair, unexpectedly, two fragments of about 414 bp and 256 bp were detected.

In the following, the nucleotide sequence (cDNA) and corresponding amino acid sequence of both fragments is provided. Numbers of positions of the nucleotides are from EGFR wild type sequence represented in SEQ ID NO:8. The corresponding protein is shown in SEQ ID NO:9.

Sequence of EGFR c.EX12__14del Fragment (414 bp) (SEQ ID NO:2)

nt 1266
AAACTGCACCTCCATCAGTGGCGATCTCCACATCCTGCCGGTGGCATTTA

GGGGTGACTCCTTCACACATACTCCTCCTCTGGATCCACAGGAACTGGAT

ATTCTGAAAACCGTAAAGGAAATCACAGGGTTTTTGCTGATT

CAGGCTTGGCCTGAAAACAGGACGGACCTCCATGCCTTTGAGAACCTAGA

AATCATACGCGGCAGGACCAAGCAACAGGACCAGACAACTGTATC

CAGTGTGCCCACTACATTGACGGCCCCACTGCGTCAAGACCAGCCCGGC

AGGAGTCATGGGAGAAAACAACACCCTGGTCTGGAAGTACGCAGACGCCG

GCCATGTGTGCCACCTGTGCCATCCAAACTGCACCTACGGATGCACTGGG

CCAGGTCTTGAAGGCTGTCCAACGAAT nt 2103 and the corresponding amino acid sequence (SEQ ID NO:5):

NCTSISGDLHILPVAFRGDSFTHTPPLDPQELDILKTVKEITGFLLIQAW

PENRTDLHAFENLEIIRGRTKQQDQTTVSSVPTTLTAPTASRPARQESWE

KTTPWSGSTQTPAMCATCAIQTAPTDALGQVLKAVQR

Therein, the underlined amino acid Q is found in exchange for H. The dotted underlined amino acids are modified due to a shift in the reading frame.

EGFR c.EX12__14del shows a frame shift in the open reading frame and a premature stop codon in exon 18 resulting in an EGFR protein with a truncated C-terminus. The frame shift results in exchange of H against Q (underlined amino acid) and completely new amino acids (dotted underlined). The following shows the amino acid sequence above which has been completed up to the stop codon in exon 18:

(SEQ ID NO: 4)
NCTSISGDLHILPVAFRGDSFTHTPPLDPQELDILKTVKEITGFLLIQAW

PENRTDLHAFENLEIIRGRTKQQDQTTVSSVPTTLTAPTASRPARQESWE

KTTPWSGSTQTPAMCATCAIQTAPTDALGQVL

KAVQRMGLRSRPSPLGWWGPSSCCWWWPWGSASSCEGATSFGSARCGGCC

RRGSLWSLLHPVEKLPTKLS*

Sequence of EGFR c.EX12__15del Fragment (256 bp) (SEQ ID NO:1)

nt 1266
AAACTGCACCTCCATCAGTGGCGATCTCCACATCCTGCCGGTGGCATTTA

GGGGTGACTCCTTCACACATACTCCTCCTCTGGATCCACAGGAACTGGAT

ATTCTGAAAACCGTAAAGGAAATCACAGGGTTTTTGCTGATTCAGGCTTG

GCCTGAAAACAGGACGGACCTCCATGCCTTTGAGAACCTAGAAATCATAC

GCGGCAGGACCAAGCAACAATGCACTGGGCCAGGTCTTGAAGGCTGTCCA

ACGAAT nt 2103 and the corresponding amino acid sequence (SEQ ID NO:3):

NCTSISGDLHILPVAFRGDSFTHTPPLDPQELDILKTVKEITGFLLIQAW

PENRTDLHAFENLEIIRGRTKQQCTGPGLEGCPTN

Again an exchange of H against Q is observed (underlined amino acid).

These fragments were isolated, cloned and sequenced with standard procedures. The sequence of the 414 bp fragment shows a deletion of exon 12 to 14 of the EGFR and the sequence of the 256 bp fragment shows a deletion of exon 12 to 15. The variants were named EGFR c.EX12__14del and EGFR c.EX12__15del, respectively. The predicted amino acid sequence of variant EGFR c.EX12__14del shows a frame shift in the open reading frame and a premature stop codon in exon 18 resulting in an EGFR protein with a truncated C-terminus. In contrast, the predicted amino acid sequence of variant EGFR c.EX12__15del shows no frame shift resulting in an EGFR with a deletion of 194 amino acids.

Further, cancer cell lines were analyzed for the variants. Both variants could be detected in breast, colon, prostate and lung carcinoma cell lines. To determine that these new variants are tumors associated, the PCR was done with cDNA of blood from 22 healthy donors and 33 colon cancer patients isolated with AdnaTest ColonCancerSelect™ (AdnaGen AG, Langenhagen, Germany) and Sensiscript Reverse Transcriptase™ (Qiagen GmbH, Hilden, Germany). None of the healthy volunteers show the variants. 2 patients show the variant EGFR c.EX12__14del and one of these patients shows the variant EGFR c.EX12__15 del additionally.

In the case of breast cancer, PCR was done with cDNA of blood from 23 healthy donors and 33 breast cancer patients with metastases (M1) isolated with AdnaTest BreastCancerSelect™ (AdnaGen AG, Langenhagen, Germany) and Sensiscript Reverse Transcriptase (Qiagen GmbH, Hilden, Germany). None of the healthy volunteers show the variants. 2 patients show the variant EGFR c.EX12__14del and 3 patients show the variant EGFR c.EX12__15del.

To summarize, the present invention provides two new molecular tumor targets. This will allow an improved detection, stratification and therapy guidance of cancer patients and have an effect on future therapy decisions. Further, these two new EGFR variants (genes and mRNA) may be used as new tumor targets for therapeutical invention, e.g. with antibodies directed against the new EGFR protein variants or antisense RNA corresponding to the respective polynucleotides. Such antibodies and antisense RNA are also comprised within this invention. With the newly discovered EGFR variants, it is possible to further analyze the patients for therapy guidance and monitoring.

What is claimed is:

1. A method for detecting the presence of a tumor in a patient comprising detecting in a tissue sample or blood from said patient a polynucleotide encoding an endothelial growth factor receptor having the sequence set forth in SEQ ID NO:2, wherein the presence of said polynucleotide indicates the presence of a tumor in said patient.

2. The method of claim 1, further comprising diagnosing, stratifying or guiding therapy of the tumor.

3. The method of claim 1, wherein the tumor is an epithelial tumor selected from the group consisting of colon cancer, lung cancer, prostate cancer, breast cancer and other solid tumors.

4. A method for detecting the presence of a tumor in a patient comprising detecting in a tissue sample or blood from said patient a polynucleotide encoding an endothelial growth factor receptor having the sequence set forth in SEQ ID NO:1, wherein the presence of said polynucleotide indicates the presence of a tumor in said patient.

5. The method of claim 4, further comprising diagnosing, stratifying or guiding therapy of the tumor.

6. The method of claim 4, wherein the tumor is an epithelial tumor selected from the group consisting of colon cancer, lung cancer, prostate cancer, breast cancer and other solid tumors.

* * * * *

SEQUENCE LISTING

<160> NUMBER OF SEQ ID NOS: 9

<210> SEQ ID NO 1
<211> LENGTH: 256
<212> TYPE: DNA
<213> ORGANISM: Homo sapiens

<400> SEQUENCE: 1
aaactgcacc tccatcagtg gcgatctcca catcctgccg gtggcattta ggggtgactc      60
cttcacacat actcctcctc tggatccaca ggaactggat attctgaaaa ccgtaaagga     120
aatcacaggg tttttgctga ttcaggcttg gcctgaaaac aggacggacc tccatgcctt     180
tgagaaccta gaaatcatac gcggcaggac caagcaacaa tgcactgggc caggtcttga     240
aggctgtcca acgaat                                                      256

<210> SEQ ID NO 2
<211> LENGTH: 414
<212> TYPE: DNA
<213> ORGANISM: Homo sapiens

<400> SEQUENCE: 2
aaactgcacc tccatcagtg gcgatctcca catcctgccg gtggcattta ggggtgactc      60
cttcacacat actcctcctc tggatccaca ggaactggat attctgaaaa ccgtaaagga     120
aatcacaggg tttttgctga ttcaggcttg gcctgaaaac aggacggacc tccatgcctt     180
tgagaaccta gaaatcatac gcggcaggac caagcaacag gaccagacaa ctgtatccag     240
tgtgcccact acattgacgg ccccccactgc gtcaagacca gccggcagg agtcatggga     300 gaaaacaaca ccctggtctg gaagtacgca gacgccggcc atgtgtgcca cctgtgccat     360
ccaaactgca cctacggatg cactgggcca ggtcttgaag ctgtccaac gaat             414

<210> SEQ ID NO 3
<211> LENGTH: 85
<212> TYPE: PRT
<213> ORGANISM: Homo sapiens

<400> SEQUENCE: 3

Asn Cys Thr Ser Ile Ser Gly Asp Leu His Ile Leu Pro Val Ala Phe
1               5                   10                  15

Arg Gly Asp Ser Phe Thr His Thr Pro Pro Leu Asp Pro Gln Glu Leu
            20                  25                  30

Asp Ile Leu Lys Thr Val Lys Glu Ile Thr Gly Phe Leu Leu Ile Gln
        35                  40                  45

Ala Trp Pro Glu Asn Arg Thr Asp Leu His Ala Phe Glu Asn Leu Glu
    50                  55                  60

Ile Ile Arg Gly Arg Thr Lys Gln Gln Cys Thr Gly Pro Gly Leu Glu
65                  70                  75                  80

Gly Cys Pro Thr Asn
            85

<210> SEQ ID NO 4
<211> LENGTH: 202
<212> TYPE: PRT
<213> ORGANISM: Homo sapiens

<400> SEQUENCE: 4

Asn Cys Thr Ser Ile Ser Gly Asp Leu His Ile Leu Pro Val Ala Phe
1               5                   10                  15

Arg Gly Asp Ser Phe Thr His Thr Pro Pro Leu Asp Pro Gln Glu Leu
            20                  25                  30

Asp Ile Leu Lys Thr Val Lys Glu Ile Thr Gly Phe Leu Leu Ile Gln
        35                  40                  45

Ala Trp Pro Glu Asn Arg Thr Asp Leu His Ala Phe Glu Asn Leu Glu
    50                  55                  60

Ile Ile Arg Gly Arg Thr Lys Gln Gln Asp Gln Thr Thr Val Ser Ser
65                  70                  75                  80

Val Pro Thr Thr Leu Thr Ala Pro Thr Ala Ser Arg Pro Ala Arg Gln
                85                  90                  95

Glu Ser Trp Glu Lys Thr Thr Pro Trp Ser Gly Ser Thr Gln Thr Pro
            100                 105                 110

Ala Met Cys Ala Thr Cys Ala Ile Gln Thr Ala Pro Thr Asp Ala Leu
        115                 120                 125

Gly Gln Val Leu Lys Ala Val Gln Arg Met Gly Leu Arg Ser Arg Pro
    130                 135                 140

Ser Pro Leu Gly Trp Trp Gly Pro Ser Ser Cys Cys Trp Trp Trp Pro
145                 150                 155                 160

Trp Gly Ser Ala Ser Cys Glu Gly Ala Thr Ser Phe Gly Ser Ala
                165                 170                 175

Arg Cys Gly Gly Cys Cys Arg Arg Gly Ser Leu Trp Ser Leu Leu His
            180                 185                 190

Pro Val Glu Lys Leu Pro Thr Lys Leu Ser
        195                 200

<210> SEQ ID NO 5
<211> LENGTH: 137
<212> TYPE: PRT
<213> ORGANISM: Homo sapiens

<400> SEQUENCE: 5

Asn Cys Thr Ser Ile Ser Gly Asp Leu His Ile Leu Pro Val Ala Phe
1               5                   10                  15

Arg Gly Asp Ser Phe Thr His Thr Pro Pro Leu Asp Pro Gln Glu Leu
            20                  25                  30

Asp Ile Leu Lys Thr Val Lys Glu Ile Thr Gly Phe Leu Leu Ile Gln
        35                  40                  45

Ala Trp Pro Glu Asn Arg Thr Asp Leu His Ala Phe Glu Asn Leu Glu
    50                  55                  60

Ile Ile Arg Gly Arg Thr Lys Gln Gln Asp Gln Thr Thr Val Ser Ser
65                  70                  75                  80

Val Pro Thr Thr Leu Thr Ala Pro Thr Ala Ser Arg Pro Ala Arg Gln
                85                  90                  95

Glu Ser Trp Glu Lys Thr Thr Pro Trp Ser Gly Ser Thr Gln Thr Pro
            100                 105                 110

Ala Met Cys Ala Thr Cys Ala Ile Gln Thr Ala Pro Thr Asp Ala Leu
        115                 120                 125

Gly Gln Val Leu Lys Ala Val Gln Arg
    130                 135

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaactgcacc tccatcagtg                                                    20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
attcgttgga cagccttcaa g                                                  21

<210> SEQ ID NO 8
<211> LENGTH: 5616
<212> TYPE: DNA
<213> ORGANISM: Homo sapiens

<400> SEQUENCE: 8

```
ccccggcgca gcgcggccgc agcagcctcc gcccccgca cggtgtgagc gcccgacgcg        60
gccgaggcgg ccggagtccc gagctagccc cggcggccgc cgccgcccag accggacgac       120
aggccacctc gtcggcgtcc gcccgagtcc ccgcctcgcc gccaacgcca caaccaccgc       180
gcacggcccc ctgactccgt ccagtattga tcgggagagc cggagcgagc tcttcgggga       240
gcagcgatgc gaccctccgg gacggccggg gcagcgctcc tggcgctgct ggctgcgctc       300
tgcccggcga gtcgggctct ggaggaaaag aaagtttgcc aaggcacgag taacaagctc       360
acgcagttgg gcacttttga agatcatttt ctcagcctcc agaggatgtt caataactgt       420
gaggtggtcc ttgggaattt ggaaattacc tatgtgcaga ggaattatga tctttccttc       480
ttaaagacca tccaggaggt ggctggttat gtcctcattg ccctcaacac agtggagcga       540
attcctttgg aaaacctgca gatcatcaga ggaaatatgt actacgaaaa ttcctatgcc       600
ttagcagtct tatctaacta tgatgcaaat aaaaccggac tgaaggagct gcccatgaga       660
aatttacagg aaatcctgca tggcgccgtg cggttcagca caaccctgc cctgtgcaac       720 gtggagagca tccagtggcg ggacatagtc agcagtgact ttctcagcaa catgtcgatg       780
gacttccaga accaccctgg gcagctgcca aagtgtgatc caagctgtcc aatgggagc       840 tgctggggtg caggagagga gaactgccag aaactgacca aaatcatctg tgcccagcag       900
tgctccgggc gctgccgtgg caagtccccc agtgactgct gccacaacca gtgtgctgca       960
ggctgcacag gccccgggga gagcgactgc ctggtctgcc gcaaattccg agacgaagcc      1020
acgtgcaagg acacctgccc cccactcatg ctctacaacc ccaccacgta ccagatggat      1080
gtgaaccccg agggcaaata cagctttggt gccacctgcg tgaagaagtg tccccgtaat      1140
tatgtggtga cagatcacgg ctcgtgcgtc cgagcctgtg gggccgacag ctatgagatg      1200
gaggaagacg gcgtccgcaa gtgtaagaag tgcgaagggc cttgccgcaa agtgtgtaac      1260
ggaataggta ttggtgaatt taaagactca ctctccataa atgctacgaa tattaaacac      1320
ttcaaaaact gcacctccat cagtggcgat ctccacatcc tgccggtggc atttaggggt      1380
gactccttca cacatactcc tcctctggat ccacaggaac tggatattct gaaaaccgta      1440
aaggaaatca cagggttttt gctgattcag gcttggcctg aaaacaggac ggacctccat      1500
gcctttgaga acctagaaat catacgcggc aggaccaagc aacatggtca gttttctctt      1560
gcagtcgtca gcctgaacat aacatccttg ggattacgct ccctcaagga gataagtgat      1620
```

```
ggagatgtga taatttcagg aaacaaaaat ttgtgctatg caaatacaat aaactggaaa      1680
aaactgtttg ggacctccgg tcagaaaacc aaaattataa gcaacagagg tgaaaacagc      1740
tgcaaggcca caggccaggt ctgccatgcc ttgtgctccc ccgagggctg ctggggcccg      1800
gagcccaggg actgcgtctc ttgccggaat gtcagccgag gcaggaatg cgtggacaag       1860 tgcaaccttc tggagggtga gccaagggag tttgtggaga actctgagtg catacagtgc      1920
cacccagagt gcctgcctca ggccatgaac atcacctgca caggacgggg accagacaac      1980
tgtatccagt gtgcccacta cattgacggc ccccactgcg tcaagacctg cccggcagga      2040
gtcatgggag aaaacaacac cctggtctgg aagtacgcag acgccggcca tgtgtgccac      2100
ctgtgccatc caaactgcac ctacggatgc actgggccag gtcttgaagg ctgtccaacg      2160
aatgggccta gatcccgtc catcgccact gggatggtgg gggccctcct cttgctgctg       2220
gtggtggccc tggggatcgg cctcttcatg cgaaggcgcc acatcgttcg gaagcgcacg      2280
ctgcggaggc tgctgcagga gagggagctt gtggagcctc ttacacccag tggagaagct      2340
cccaaccaag ctctcttgag gatcttgaag gaaactgaat tcaaaaagat caaagtgctg      2400
ggctccggtg cgttcggcac ggtgtataag ggactctgga tcccagaagg tgagaaagtt      2460
aaaattcccg tcgctatcaa ggaattaaga gaagcaacat ctccgaaagc caacaaggaa      2520
atcctcgatg aagcctacgt gatggccagc gtggacaacc cccacgtgtg ccgcctgctg      2580
ggcatctgcc tcacctccac cgtgcagctc atcacgcagc tcatgccctt cggctgcctc      2640
ctggactatg tccgggaaca caaagacaat attggctccc agtacctgct caactggtgt      2700
gtgcagatcg caaagggcat gaactacttg gaggaccgtc gcttggtgca ccgcgacctg      2760
gcagccagga cgtactggt gaaaacaccg cagcatgtca agatcacaga ttttgggctg      2820
gccaaactgc tgggtgcgga agagaaagaa taccatgcag aaggaggcaa agtgcctatc      2880
aagtggatgg cattggaatc aattttacac agaatctata cccaccagag tgatgtctgg      2940
agctacgggg tgaccgtttg ggagttgatg acctttggat ccaagccata tgacggaatc      3000
cctgccagcg agatctcctc catcctggag aaaggagaac gcctccctca gccacccata      3060
tgtaccatcg atgtctacat gatcatggtc aagtgctgga tgatagacgc agatagtcgc      3120
ccaaagttcc gtgagttgat catcgaattc tccaaaatgg cccgagaccc ccagcgctac      3180
cttgtcattc aggggatga agaatgcat ttgccaagtc ctacagactc caacttctac       3240
cgtgccctga tggatgaaga agacatggac gacgtggtgg atgccgacga gtacctcatc      3300
ccacagcagg gcttcttcag cagccctcc acgtcacgga ctcccctcct gagctctctg       3360
agtgcaacca gcaacaattc caccgtggct tgcattgata gaaatgggct gcaaagctgt      3420
cccatcaagg aagacagctt cttgcagcga tacagctcag accccacagg cgccttgact      3480
gaggacagca tagacgacac cttcctccca gtgcctgaat acataaacca gtccgttccc      3540
aaaaggcccg ctggctctgt gcagaatcct gtctatcaca atcagcctct gaaccccgcg      3600
cccagcagag acccacacta ccaggacccc cacagcactg cagtgggcaa cccgagtat      3660 ctcaacactg tccagcccac ctgtgtcaac agcacattcg acagccctgc ccactgggcc      3720
cagaaaggca gccaccaaat tagcctggac aaccctgact accagcagga cttctttccc      3780
aaggaagcca agccaaatgg catctttaag ggctccacag ctgaaaatgc agaatacctg      3840
agggtcgcgc cacaaaagcag tgaatttat ggagcatgac cacggaggat agtatgagcc      3900
ctaaaaatcc agactctttc gatacccagg accaagccac agcaggtcct ccatcccaac      3960
agccatgccc gcattagctc ttagacccac agactggttt tgcaacgttt acaccgacta      4020
```

-continued

```
gccaggaagt acttccacct cgggcacatt ttgggaagtt gcattccttt gtcttcaaac    4080
tgtgaagcat ttacagaaac gcatccagca agaatattgt cccttttgagc agaaatttat   4140 ctttcaaaga ggtatatttg aaaaaaaaaa aaagtatatg tgaggatttt tattgattgg    4200
ggatcttgga gttttttcatt gtcgctattg attttttactt caatgggctc ttccaacaag  4260
gaagaagctt gctggtagca cttgctaccc tgagttcatc caggcccaac tgtgagcaag    4320
gagcacaagc cacaagtctt ccagaggatg cttgattcca gtggttctgc ttcaaggctt    4380
ccactgcaaa acactaaaga tccaagaagg ccttcatggc cccagcaggc cggatcggta    4440
ctgtatcaag tcatggcagg tacagtagga taagccactc tgtcccttcc tgggcaaaga    4500
agaaacggag gggatggaat tcttccttag acttactttt gtaaaaatgt ccccacggta    4560
cttactcccc actgatggac cagtggtttc cagtcatgag cgttagactg acttgtttgt    4620
cttccattcc attgttttga aactcagtat gctgcccctg tcttgctgtc atgaaatcag    4680
caagagagga tgacacatca ataataact cggattccag cccacattgg attcatcagc    4740
atttggacca atagcccaca gctgagaatg tggaataccct aaggatagca ccgcttttgt   4800
tctcgcaaaa acgtatctcc taatttgagg ctcagatgaa atgcatcagg tcctttgggg    4860
catagatcag aagactacaa aaatgaagct gctctgaaat ctcctttagc catcacccca    4920
accccccaaa attagtttgt gttacttatg gaagatagtt ttctccttttt acttcacttc   4980 aaaagctttt tactcaaaga gtatatgttc cctccaggtc agctgccccc aaaccccctc    5040
cttacgcttt gtcacacaaa aagtgtctct gccttgagtc atctattcaa gcacttacag    5100
ctctggccac aacagggcat tttacaggtg cgaatgacag tagcattatg agtagtgtgg    5160
aattcaggta gtaaatatga aactagggtt tgaaattgat aatgctttca caacatttgc    5220
agatgtttta gaaggaaaaa agttccttcc taaaataatt tctctacaat tggaagattg    5280
gaagattcag ctagttagga gcccacctttt tttcctaatc tgtgtgtgcc ctgtaacctg   5340
actggttaac agcagtcctt tgtaaacagt gtttttaaact ctcctagtca atatccaccc   5400
catccaattt atcaaggaag aaatggttca gaaaatattt tcagcctaca gttatgttca    5460
gtcacacaca catacaaaat gttccttttg cttttaaagt aatttttgac tcccagatca    5520
gtcagagccc ctacagcatt gttaagaaag tatttgattt ttgtctcaat gaaaataaaa    5580
ctatattcat ttccactcta aaaaaaaaaa aaaaaa                              5616
```

<210> SEQ ID NO 9
<211> LENGTH: 1210
<212> TYPE: PRT
<213> ORGANISM: Homo sapiens

<400> SEQUENCE: 9

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95
```

-continued

```
Glu Arg Ile Pro Leu Glu Asn Leu Gln Ile Ile Arg Gly Asn Met Tyr
                100                 105                 110
Tyr Glu Asn Ser Tyr Ala Leu Ala Val Leu Ser Asn Tyr Asp Ala Asn
            115                 120                 125
Lys Thr Gly Leu Lys Glu Leu Pro Met Arg Asn Leu Gln Glu Ile Leu
        130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
        195                 200                 205
Lys Leu Thr Lys Ile Ile Cys Ala Gln Gln Cys Ser Gly Arg Cys Arg
210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
        290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
```

-continued

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys

-continued

```
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
                980                 985                 990
Thr Asp Ser Asn Phe Tyr Arg Ala Leu Met Asp Glu Glu Asp Met Asp
                995                 1000                1005
Asp Val Val Asp Ala Asp Glu Tyr Leu Ile Pro Gln Gln Gly Phe
    1010                1015                1020
Phe Ser Ser Pro Ser Thr Ser Arg Thr Pro Leu Leu Ser Ser Leu
    1025                1030                1035
Ser Ala Thr Ser Asn Asn Ser Thr Val Ala Cys Ile Asp Arg Asn
    1040                1045                1050
Gly Leu Gln Ser Cys Pro Ile Lys Glu Asp Ser Phe Leu Gln Arg
    1055                1060                1065
Tyr Ser Ser Asp Pro Thr Gly Ala Leu Thr Glu Asp Ser Ile Asp
    1070                1075                1080
Asp Thr Phe Leu Pro Val Pro Glu Tyr Ile Asn Gln Ser Val Pro
    1085                1090                1095
Lys Arg Pro Ala Gly Ser Val Gln Asn Pro Val Tyr His Asn Gln
    1100                1105                1110
Pro Leu Asn Pro Ala Pro Ser Arg Asp Pro His Tyr Gln Asp Pro
    1115                1120                1125
His Ser Thr Ala Val Gly Asn Pro Glu Tyr Leu Asn Thr Val Gln
    1130                1135                1140
Pro Thr Cys Val Asn Ser Thr Phe Asp Ser Pro Ala His Trp Ala
    1145                1150                1155
Gln Lys Gly Ser His Gln Ile Ser Leu Asp Asn Pro Asp Tyr Gln
    1160                1165                1170
Gln Asp Phe Phe Pro Lys Glu Ala Lys Pro Asn Gly Ile Phe Lys
    1175                1180                1185
Gly Ser Thr Ala Glu Asn Ala Glu Tyr Leu Arg Val Ala Pro Gln
    1190                1195                1200
Ser Ser Glu Phe Ile Gly Ala
    1205                1210
```